US010561358B2

(12) United States Patent
Nakayama et al.

(10) Patent No.: US 10,561,358 B2
(45) Date of Patent: *Feb. 18, 2020

(54) BIOMETRIC DEVICE AND BIOMETRIC METHOD

(71) Applicant: PANASONIC INTELLECTUAL PROPERTY MANAGEMENT CO., LTD., Osaka (JP)

(72) Inventors: Takeshi Nakayama, Hyogo (JP); Shoichi Iizuka, Osaka (JP); Naoki Honma, Iwate (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/537,178

(22) Filed: Aug. 9, 2019

(65) Prior Publication Data

US 2019/0357835 A1 Nov. 28, 2019

Related U.S. Application Data

(63) Continuation of application No. 15/667,437, filed on Aug. 2, 2017, now Pat. No. 10,413,229.

(30) Foreign Application Priority Data

Aug. 29, 2016 (JP) .................................. 2016-167260
Apr. 28, 2017 (JP) .................................. 2017-090545

(51) Int. Cl.
*A61B 5/18* (2006.01)
*A61B 5/05* (2006.01)
(Continued)

(52) U.S. Cl.
CPC .............. *A61B 5/18* (2013.01); *A61B 5/0077* (2013.01); *A61B 5/02405* (2013.01); *A61B 5/05* (2013.01);
(Continued)

(58) Field of Classification Search
CPC combination set(s) only.
See application file for complete search history.

(56) References Cited

U.S. PATENT DOCUMENTS

| 7,194,752 B1 | 3/2007 | Kenyon et al. |
| 2007/0156317 A1 | 7/2007 | Breed |

(Continued)

FOREIGN PATENT DOCUMENTS

| JP | 2005-314847 A | 11/2005 |
| JP | 2007-325621 A | 12/2007 |

(Continued)

OTHER PUBLICATIONS

Extended European Search Report, dated Dec. 1, 2017, from the European Patent Office (EPO) for the related European Patent Application No. 17184832.8.

(Continued)

*Primary Examiner* — An T Nguyen
(74) *Attorney, Agent, or Firm* — Greenblum & Bernstein, P.L.C.

(57) ABSTRACT

A device differentiates a living body, the device including a circuit. The circuit acquires first N reception signals, each of the first N reception signals has been received at respective one receiver out of N receivers, which are arranged to surround a periphery of a predetermined range, using respective reception antenna elements of the N receivers during a predetermined period. The circuit also calculates a plurality of correlation coefficients based on a teacher signal, stored in the memory, and the first N reception signals. The circuit further determines that the living body and a subject living body are identical to each other when a correlation coefficient, included in the plurality of correlation coefficients, is included in a predetermined value range.

8 Claims, 11 Drawing Sheets

(51) Int. Cl.
*A61B 5/117* (2016.01)
*A61B 5/00* (2006.01)
*A61B 5/024* (2006.01)
*A61B 5/11* (2006.01)

(52) U.S. Cl.
CPC .............. *A61B 5/11* (2013.01); *A61B 5/117* (2013.01); *A61B 5/6893* (2013.01); *A61B 5/74* (2013.01); *A61B 5/00* (2013.01)

(56) References Cited

U.S. PATENT DOCUMENTS

| | | | |
|---|---|---|---|
| 2010/0214154 A1* | 8/2010 | Birdsong, Jr. | G01S 7/282 342/90 |
| 2013/0093616 A1* | 4/2013 | Jeon | G01S 7/412 342/118 |
| 2013/0113653 A1* | 5/2013 | Kishigami | G01S 7/285 342/189 |
| 2015/0309167 A1 | 10/2015 | Shikatani et al. | |
| 2018/0373391 A1* | 12/2018 | Cortes | G06F 3/017 |

FOREIGN PATENT DOCUMENTS

| | | |
|---|---|---|
| JP | 2009-055997 A | 3/2009 |
| JP | 2015-042293 A | 3/2015 |
| WO | 2006/048701 A2 | 5/2006 |
| WO | 2016/183380 A1 | 11/2016 |

OTHER PUBLICATIONS

Communication pursuant to Article 94(3) EPC, dated Nov. 23, 2018, from the European Patent Office (EPO) for the related European Patent Application No. 17184832.8.

* cited by examiner

BIOMETRIC DEVICE AND BIOMETRIC METHOD

This application is a Continuation of U.S. patent application Ser. No. 15/667,437, filed on Aug. 2, 2017, which claims priority to Japanese Application No.: 2017-090545, filed on Apr. 28, 2017 and Japanese Application No.: 2016-167260, filed on Aug. 29, 2016, the entire disclosures of which Applications are incorporated by reference herein.

BACKGROUND

1. Technical Field

The present disclosure relates to biometric devices and biometric methods that differentiate living bodies by irradiating living bodies with radio signals and receiving reflection signals thereof.

2. Description of the Related Art

For example, Japanese Unexamined Patent Application Publication No. 2015-042293 discloses a device that differentiates an individual by irradiating the driver of an automobile with electromagnetic waves and extracting cardiac beats and cardiac sound signals using reflection waves of the electromagnetic waves.

Further, Japanese Unexamined Patent Application Publication No. 2009-055997 discloses a method of measuring the heart rate of a subject person using a plurality of transmitters and receivers with respect to the driver of an automobile.

In addition, Japanese Unexamined Patent Application Publication No. 2007-325621 discloses a 360-degree radiation pattern measurement device that uses a plurality of antennas with respect to a subject person.

The above-described conventional techniques, however, need further improvement.

SUMMARY

In one general aspect, the techniques disclosed here feature a device that differentiates a living body, the device including: at least one transmission antenna element that transmits a transmission signal to a predetermined range including the living body; N receivers that are arranged to surround a periphery of the predetermined range and each receive N reception signals using respective reception antenna elements of the receivers during a predetermined period, the N reception signals including a reflection signal resulting from the transmission signal reflected off the living body; memory that stores a teacher signal constituted of N reception signals obtained by the N receivers receiving in advance reception signals including a reflection signal resulting from a transmission signal that is transmitted from the at least one transmission antenna element to a subject living body and then reflected off the subject living body; a circuit that calculates a plurality of correlation coefficients according to the teacher signal and the N reception signals obtained by being received by the N receivers and determines that the living body and the subject living body are identical to each other when a predetermined correlation coefficient included in the plurality of correlation coefficients is included in a predetermined value range.

The biometric device according to the present disclosure can increase flexibility in living body discrimination and perform living body discrimination effectively in a short time.

These general or specific aspects may be implemented as a system, a method, an integrated circuit, a computer program, a recording medium, such as a computer-readable compact disc read-only memory (CD-ROM), or any given combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
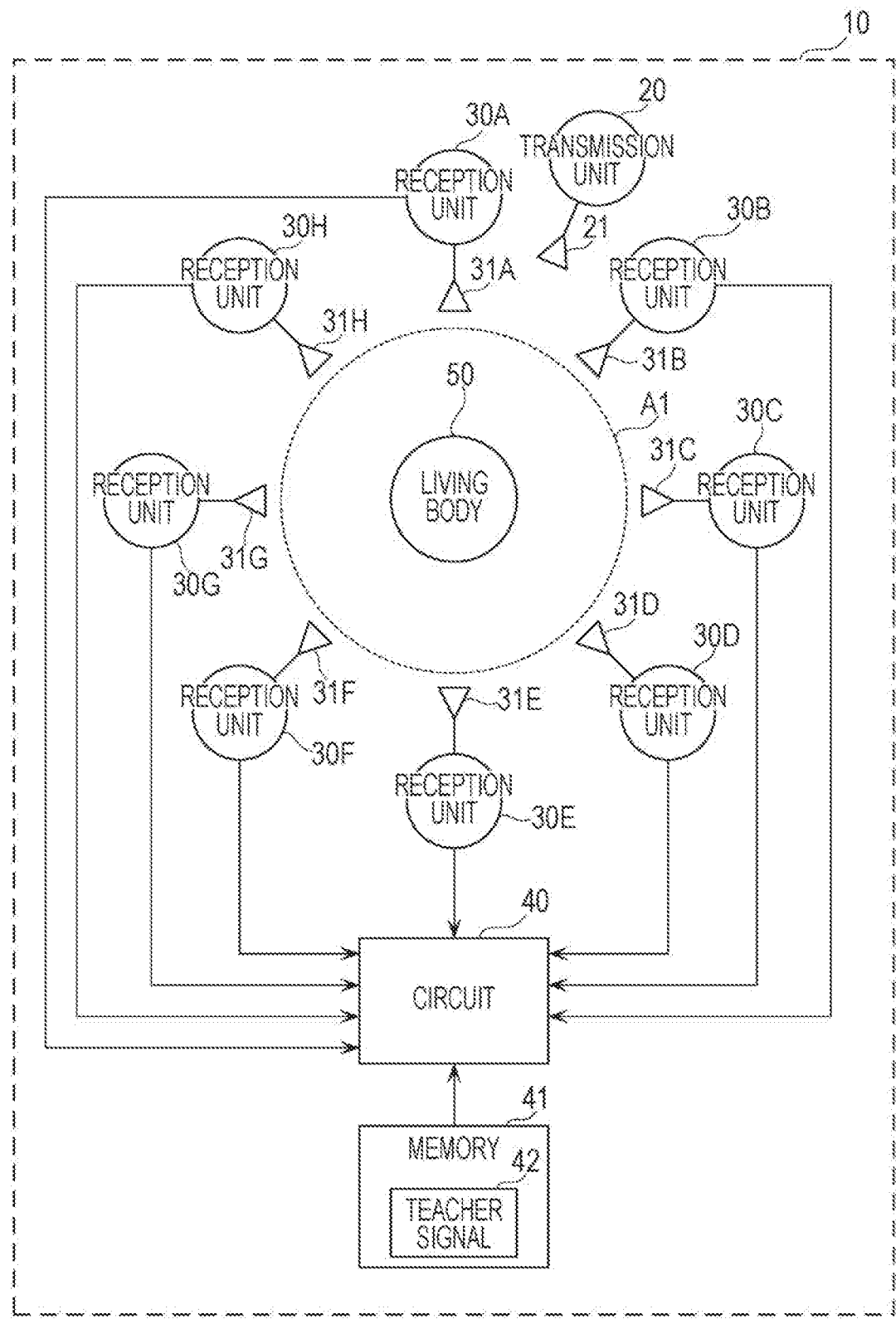
FIG. 1 is a configuration diagram that illustrates an example of a configuration of a biometric device according to a first embodiment.

Underlying Knowledge Forming Basis of Present Disclosure

The present inventors have reviewed conventional techniques in detail that are related to living body discrimination and utilize electromagnetic waves. In the methods according to Japanese Unexamined Patent Application Publication No. 2015-042293 and Japanese Unexamined Patent Application Publication No. 2009-055997, a person sitting in the driver's seat of an automobile is irradiated with electromagnetic waves and reflection waves from the person are measured, and a computation process is performed on the results of the measurement. Cardiac beats or cardiac sounds are measured through the computation process and temporal correlation of the measured cardiac beats or cardiac sounds are obtained to implement living body discrimination. In addition to the situation where a human is sitting in the driver's seat, however, there are many other situations that need living body discrimination and living body discrimination in various situations, such as those where a human is standing up, sitting down, sleeping, or walking, is not sufficiently considered.

The present inventors have redoubled studies to address the above-described problem, and consequently reached the thought that in order to widen the sphere of application of a biometric device that differentiates a living body, it is necessary to increase flexibility of a distance or a positional relation between an antenna and a subject living body of the living body discrimination to reduce constraints between the antenna and the subject living body. Specifically, the present inventors have found that in order to increase flexibility of the orientation of a subject living body, that is, in order to be capable of differentiating a subject living body in whichever direction the subject living body is oriented, it is desirable that antennas be arranged to be oriented toward the subject living body at a plurality of positions based around the subject living body. Also, the present inventors have found that in order to increase flexibility of the distance between an antenna and a subject living body, conditions of the distance between the subject living body and the antenna can be eased by measuring the position of the subject living body and performing distance correction using the result of the measurement. Further, the present inventors have found that as the distance between a subject living body and an antenna increases, reflection waves from the subject living body received at the antenna weaken and thus, it is desirable that measurement time be sufficiently lengthened to for example, several tens of seconds. In addition, the present inventors have found that accidental coincidences or noise components can be removed by increasing the number of pieces of data to be obtained, obtaining a plurality of patterns of temporal correlation, sorting results of the obtained patterns of temporal correlation in descending order, and differentiating a living body when the results are included in a predetermined region. The present inventors have conceived the present disclosure through such findings.

(1) A device according to an aspect of the present disclosure is a device that differentiates a living body, the device including: at least one transmission antenna element that transmits a transmission signal to a predetermined range including the living body; N receivers that are arranged to surround a periphery of the predetermined range and each receive N reception signals using respective reception antenna elements of the receivers during a predetermined period, the N reception signals including a reflection signal resulting from the transmission signal reflected off the living body; memory that stores a teacher signal constituted of N reception signals obtained by the N receivers receiving in advance reception signals including a reflection signal resulting from a transmission signal that is transmitted from the at least one transmission antenna element to a subject living body and then reflected off the subject living body; a circuit that calculates a plurality of correlation coefficients according to the teacher signal and the N reception signals obtained by being received by the N receivers and determines that the living body and the subject living body are identical to each other when a predetermined correlation coefficient included in the plurality of correlation coefficients is included in a predetermined value range.

According to the aspect, living body discrimination is performed using the reception signals received by the N receivers arranged to surround the periphery of the predetermined range. Thus, regardless of the orientation of a living body, living body discrimination can be performed with a small number of times of measurement. As a result, flexibility of living body discrimination can be increased and the living body discrimination can be performed effectively in a short time.

(2) In the above-described aspect, the circuit may further calculate a cumulative distribution function with respect to the plurality of correlation coefficients, and determine that the living body and the subject living body are identical to each other when a correlation coefficient that is included in the plurality of correlation coefficients and has a cumulative percentage that indicates a first value in the cumulative distribution function is included in a value range not less than a second value and not more than a third value.

Thus, living body discrimination can be performed more accurately.

(3) In the above-described aspect, the circuit may calculate a plurality of correlation coefficients between the teacher signal and each of the N reception signals as the plurality of correlation coefficients by sliding correlation operation.

Thus, living body discrimination can be performed effectively.

(4) In the above-described aspect, the circuit may further estimate a position of the living body in the predetermined range using the N reception signals, and calculate the plurality of correlation coefficients using the position of the living body.

Thus, living body discrimination can be performed effectively according to the position of a living body.

(5) In the above-described aspect, the at least one transmission antenna element may include a plurality of transmission antenna elements, and the plurality of transmission antenna elements may be arranged at positions different from each other.

Thus, reception signals can be obtained, the number of which is the number decided through multiplication by the number of a plurality of transmitters. Accordingly, the number of correlation coefficients can be increased and living body discrimination can be performed accurately in a short time.

(6) In the above-described aspect, the at least one transmission antenna element may include N transmission antenna elements, the N reception antenna elements may be respectively the N transmission antenna elements, and the circuit may further estimate a position of the living body in the predetermined range using the N reception signals, and calculate the plurality of correlation coefficients using the position of the living body.

Thus, the N transmission antenna elements and the N reception antenna elements can double as each other and the configuration of the biometric device can be simplified.

(7) In the above-described aspect, the teacher signal may be constituted of the N reception signals obtained by the N receivers receiving the reception signals in advance during a period that is K times as long as the predetermined period, where K is two or more.

Thus, living body discrimination can be performed more accurately.

Embodiments of the present disclosure are described in detail below by referring to the drawings. All of the embodiments described below present desirable specific examples of the present disclosure. The values, shapes, materials, constituents, arrangement positions of the constituents, connection forms, steps, orders of the steps, and the like that are mentioned below in the embodiments are examples and are not intended to limit the present disclosure. Among the constituents of the embodiments below, the constituents that are not recited in independent claims indicating the most superordinate concepts of the present disclosure can be explained as given constituents that form more desirable embodiments. In the present specification and drawings, as for the constituents that have substantially identical functional configurations, overlapping descriptions are omitted by providing identical references.

First Embodiment

FIG. 1 is a configuration diagram that illustrates an example of a configuration of a biometric device 10 according to a first embodiment.

As illustrated in FIG. 1, the biometric device 10 includes a transmission unit 20, N reception units, which are reception units 30A to 30H in the present embodiment, a circuit 40, and memory 41. The biometric device 10 transmits a transmission signal from the transmission unit 20 to a predetermined range A1 including a living body 50, such as a human, and receives reception signals including reflection signals, which are reflected off the living body 50, at the reception units 30A to 30H. The biometric device 10 differentiates the living body 50 by the circuit 40 processing the reception signals received by the reception units 30A to 30H.

The transmission unit 20 includes at least one transmission antenna element 21. The transmission antenna element 21 transmits a transmission signal to the predetermined range A1. The transmission unit 20 may be arranged at a position around the predetermined range A1, that is, a position outside the predetermined range A1. Specifically, the transmission antenna element 21 emits microwaves as a transmission signal to the living body 50, such as a human. The transmission antenna element 21 may transmit an unmodulated transmission signal or may transmit a modulated transmission signal. When modulation is performed, the transmission unit 20 may include a circuit for performing the modulation. The transmission antenna element 21 is arranged at a position around the predetermined range A1. The predetermined range A1 is space in a predetermined range for the biometric device 10 to differentiate the living body 50.

Each of the reception units 30A to 30H includes corresponding one of reception antenna elements 31A to 31H. The reception antenna elements 31A to 31H receive reception signals including reflection signals, which are signals transmitted from the transmission unit 20 and then reflected off the living body 50, during a predetermined period. The reception units 30A to 30H are arranged in a circle at regular intervals between each other, for example, while surrounding the periphery of the predetermined range A1. The reception units 30A to 30H are constituted of N reception units, where N is eight in the present embodiment.

Each of the reception units 30A to 30H may perform frequency conversion on a reception signal to convert the reception signal into a low-frequency signal. Each of the reception units 30A to 30H may perform a demodulation process on a reception signal. Each of the reception units 30A to 30H outputs a signal obtained through the frequency conversion and/or the demodulation process to the circuit 40. Each of the reception units 30A to 30H may include a circuit for processing a reception signal.

The circuit 40 executes various processes to operate the biometric device 10. The circuit 40 is constituted of, for example, a processor that executes a control program and a volatile storage area (a main storage device) utilized as a work area used in executing the control program. The volatile storage area is random access memory (RAM) for example.

The circuit 40 causes a signal obtained from each of the reception units 30A to 30H to be temporarily stored in the volatile storage area for a predetermined period. The circuit 40 may cause the phase and amplitude of the signal to be temporarily stored in the volatile storage area for a predetermined period. The circuit 40 may include a nonvolatile storage area and may cause the signal to be temporarily stored in the nonvolatile storage area for a predetermined period.

The circuit 40 may be constituted of a dedicated circuit for performing various processes to operate the biometric device 10. That is, the circuit 40 may be a circuit that performs a software process or may be a circuit that performs a hardware process.

The memory 41 is a nonvolatile storage area (an auxiliary storage device), such as ROM, flash memory, or a hard disk drive (HDD). For example, the memory 41 stores information utilized for various processes to operate the biometric device 10.

Figure 2:
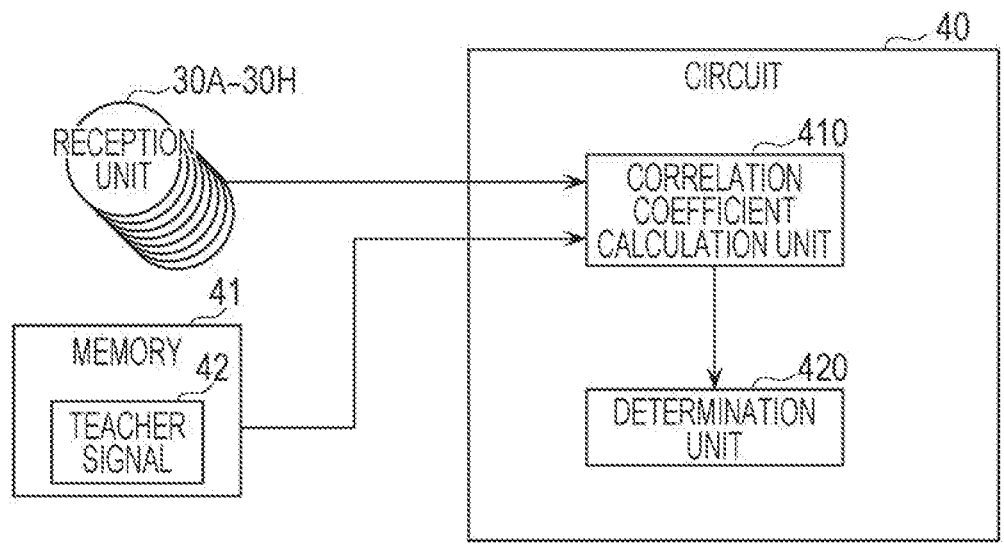
FIG. 2 is a block diagram that illustrates functional configurations of a circuit and memory according to the first embodiment.

Referring now to FIG. 2, a functional configuration of the circuit 40 is described.

FIG. 2 is a block diagram that illustrates functional configurations of the circuit 40 and the memory 41 according to the first embodiment.

The circuit 40 includes a correlation coefficient calculation unit 410 and a determination unit 420.

The correlation coefficient calculation unit 410 calculates a plurality of correlation coefficients by comparing a teacher signal 42 stored in the memory 41 and N reception signals received and obtained by the reception units 30A to 30H. The N reception signals to be compared are signals that are stored in the storage area of the circuit 40 for a predetermined period.

The teacher signal 42 stored in the memory 41 is described below.

Figure 3:
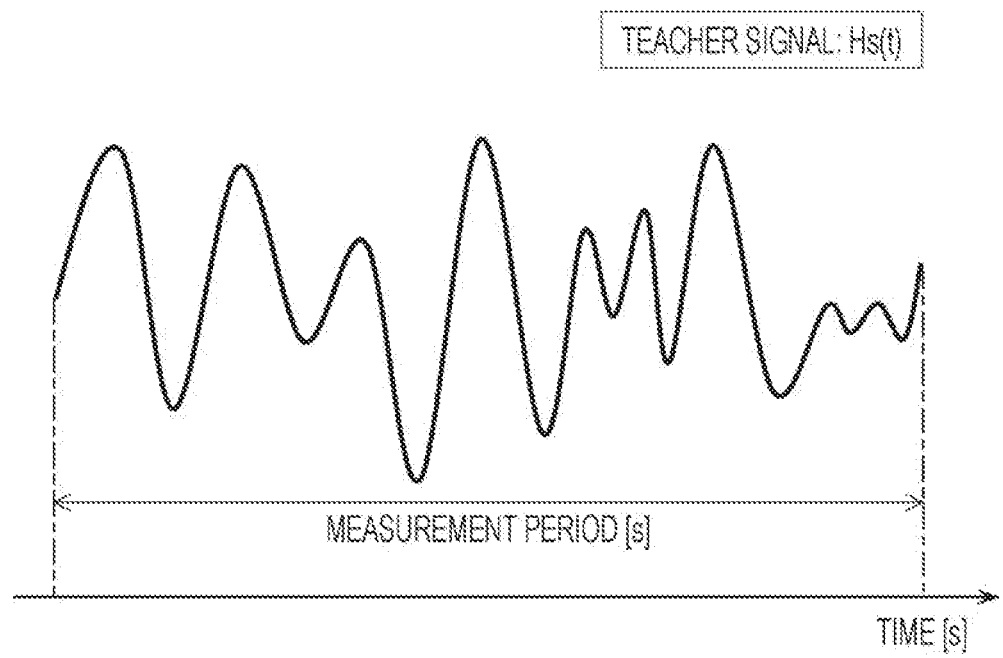
FIG. 3 is an example of a teacher signal.

FIG. 3 is an example of the teacher signal 42.

The teacher signal 42 indicates a time response waveform of the N reception signals obtained by the reception units 30A to 30H receiving reception signals in advance, which include reflection signals resulting from transmission signals transmitted from the transmission antenna element 21 to an already-known subject living body present in the predetermined range A1, such as a human, and then reflected off the surface of the subject living body. That is, as illustrated in FIG. 3, the teacher signal 42 is constituted of N reception signals obtained by the reception units 30A to 30H receiving reception signals in advance, which include reflection signals during a period that is K times as long as a predetermined period for differentiating the living body 50 (see the measurement period in FIG. 3), where K is 2 or more. The measurement period is 120 seconds [s] for example. The teacher signal illustrated in FIG. 3 is an example of reception signals received by one reception unit.

The teacher signal 42 may be obtained in advance for each of a plurality of already-known subject living bodies. In this case, the plurality of teacher signals 42 that respectively correspond to the plurality of already-known subject living bodies are each stored in the memory 41 while related to discrimination information to differentiate the corresponding subject living bodies.

Specifically, the correlation coefficient calculation unit 410 calculates a plurality of correlation coefficients between the teacher signal 42 and the N reception signals through a sliding correlation operation. The sliding correlation operation performed here is a computation expressed by the following expression:

$$\rho_l(\tau, k) = \frac{\int_0^T S_l^H(t) C^k S(t-\tau) dt}{\sqrt{\int_0^T \|S_l(t)\|_F^2 dt} \sqrt{\int_0^T \|S(t)\|_F^2 dt}} \quad (1)$$

to determine a correlation coefficient.

$$S_l(t) = [s_{l1}(t), \ldots, s_{lM}(t)]^T \quad (2)$$

$$S(t) = [s_1(t), \ldots, s_M(t)]^T \quad (3)$$

$$C = \begin{bmatrix} 0 & 1 & 0 & \cdots & 0 \\ \vdots & 0 & 1 & \ddots & \vdots \\ & & 0 & \ddots & 0 \\ 0 & & \vdots & \ddots & 1 \\ 1 & 0 & 0 & \cdots & 0 \end{bmatrix} \quad (4)$$

In expressions (2) to (4), $S_l(t)$ represents an l-th teacher complex signal vector, $S(t)$ represents an observed complex signal vector, and C represents a cyclic permutation matrix. Further, $k(0 \le k \le M-1)$ represents an exponent of the cyclic permutation matrix and corresponds to the orientation of a living body. That is, when multiplied by C one time, an element of an observation signal vector S is cyclically shifted by one row and accordingly, it is equivalent that the whole reception antenna is rotated 360/M degrees on the basis of the center of the circle. As for $C^k$, the reception antenna is rotated 360 k/M degrees and this is for enabling a living body to be recognized even if the living body turns in a given direction. Further, τ is for consideration of a time difference between a reception signal and a teacher signal observed. This is for utilizing that waveform responses caused by a living body are cyclic, and changing τ enables a reception signal observed at a given timing to be compared with a teacher signal observed while slid. The correlation coefficient calculation unit 410 calculates the maximum value of a correlation coefficient, $$\rho = \underset{0 \le \tau \le \tau_{max}, 0 \le k \le M-1}{\operatorname{argmax}} \rho_l(\tau, k) \quad (5)$$

by changing τ and k described above. In expression (5), $\tau_{max}$ represents the maximum time difference in performing the sliding correlation operation and is desirably set to match a cycle of living body activities or to be longer than or equal to approximately a few times as long as the cycle. When for example, a cycle of respiration is three seconds, $\tau_{max}$ is desirably set to be not less than three times as long, that is, to approximately ten seconds. When teacher signals are measured for an already-known living body beforehand over and over again and the memory 41 stores a plurality of teacher signals concerning the already-known living body, many correlation coefficients ρ may be obtained at a single observation by performing the computation in expression (5) on the plurality of teacher signals. The teacher complex signal vector $S_l(t)$ and the complex signal vector $S(t)$ may be propagation channels (transfer functions) between the transmission antenna element 21 and each of the reception antenna elements 31A to 31H.

The determination unit 420 determines whether the plurality of correlation coefficients calculated by the correlation coefficient calculation unit 410 are included in a predetermined value range. When a predetermined correlation coefficient among the plurality of correlation coefficients is included in the predetermined value range, the determination unit 420 determines that the living body 50 and the subject living body are identical.

Specifically, the determination unit 420 calculates a cumulative distribution function with respect to the plurality of correlation coefficients. The determination unit 420 determines whether, among the plurality of correlation coefficients, a correlation coefficient with a cumulative percentage that has a first value in the calculated cumulative distribution function is included in a value range not less than a second value. When as a result, it is determined that a correlation coefficient with a cumulative percentage that has the first value in the calculated cumulative distribution function is included in the value range not less than the second value, the determination unit 420 determines that the living body 50 and the subject living body are identical.

Although the determination unit 420 determines that the living body 50 and the subject living body are identical when a correlation coefficient with a cumulative percentage that has the first value in the calculated cumulative distribution function is included in the value range not less than the second value, the criterion of the determination is not limited to the value range not less than the second value. The determination unit 420 may determine that the living body 50 and the subject living body are identical when the correlation coefficient is included in a value range not less than the second value and not more than a third value. The determination unit 420 may determine that the living body 50 and the subject living body are identical when the correlation coefficient is included in a value range not more than the third value.

When the plurality of teacher signals 42 obtained in advance respectively for the plurality of already-known subject living bodies are stored in the memory 41, each of the teacher signals 42 corresponding to the plurality of subject living bodies is processed in the circuit 40. Accordingly, the circuit 40 differentiates the living body 50 as the subject living body corresponding to the teacher signal 42 determined as being identical to the living body 50.

Figure 4:
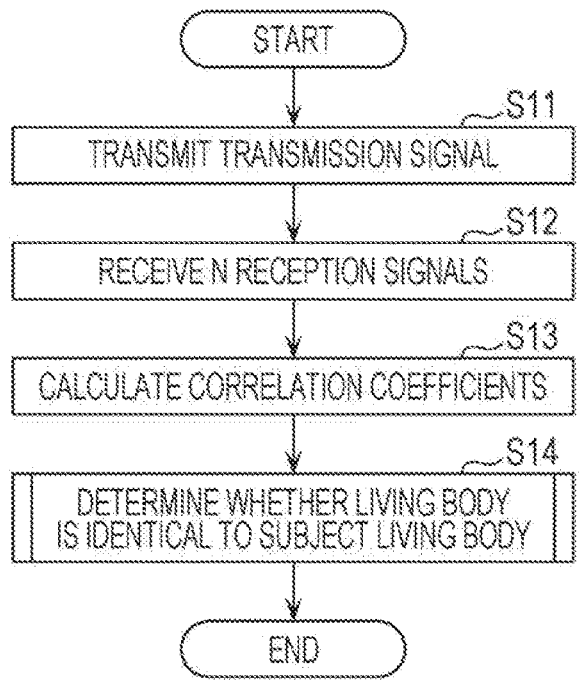
FIG. 4 is a flow chart that illustrates an example of operations of the biometric device according to the first embodiment.

FIG. 4 is a flow chart that illustrates an example of operations of the biometric device 10 according to the first embodiment.

In the biometric device 10, while the living body 50 is located in the predetermined range A1, the transmission antenna element 21 transmits a transmission signal to the predetermined range A1 (S11).

The reception units 30A to 30H receive reception signals including reflection signals, which result from transmission signals reflected off the living body 50, using the respective reception antenna elements 31A to 31H of the reception units 30A to 30H during a predetermined period (S12).

The circuit 40 reads the teacher signal 42 out of the memory 41 and calculates a plurality of correlation coefficients on the basis of the read teacher signal 42 and N reception signals (S13). Specifically, with respect to the complex signal vector S(t) obtained by processing the obtained reception signals, the circuit 40 determines the correlation coefficients through the procedures of expressions (1) to (5). It is here assumed that L teacher signal groups $[S_1(t), \ldots, S_L(t)]$, which are obtained by performing an observation of the teacher complex signal vector $S_l(t)$ during certain time T by L times in advance, are stored in the memory 41. In this case, since the correlation coefficients are determined by comparing the L teacher signal groups and the N reception signals, the number of correlation coefficients to be obtained is L×N.

After that, when a predetermined correlation coefficient among the plurality of correlation coefficients calculated is included in a predetermined value range, the circuit 40 determines that the living body 50 and the subject living body are identical (S14).

The determination process in step S14 is specifically described below.

Figure 5:
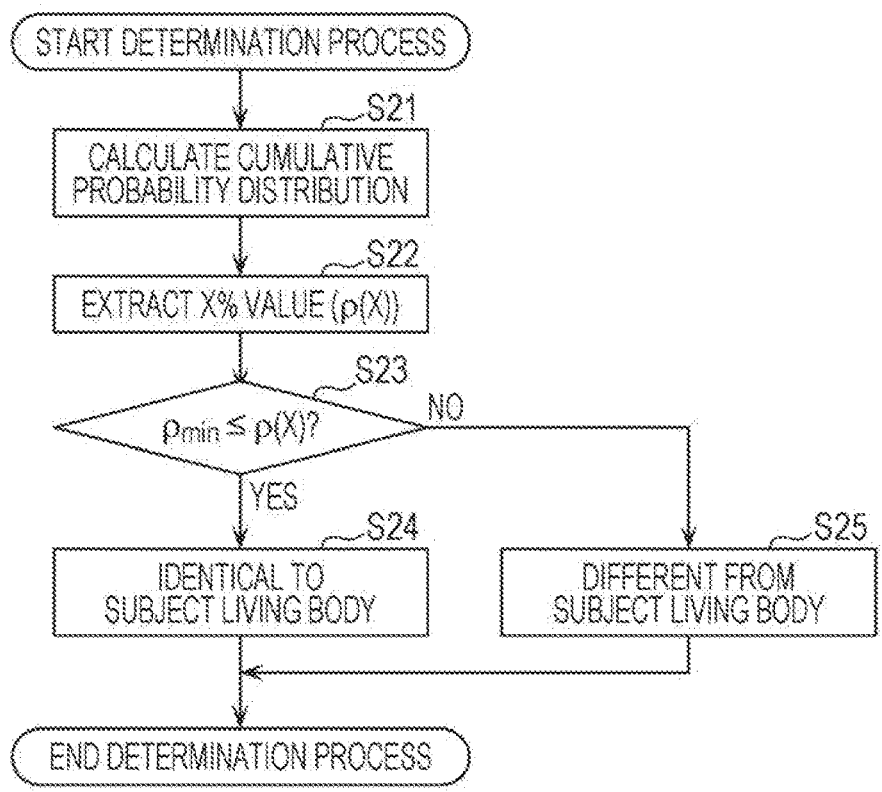
FIG. 5 is a flow chart that illustrates an example of the determination process according to the first embodiment.

FIG. 5 is a flow chart that illustrates an example of the determination process according to the first embodiment.

In the determination process, the determination unit 420 calculates cumulative probability distribution of a plurality of correlation coefficients (S21).

The determination unit 420 calculates a correlation coefficient $\rho(X)$ included in the plurality of correlation coefficients and having a cumulative percentage that is an X % value as a first value in the calculated cumulative probability distribution (S22). In the determination unit 420, a discrimination rate described below can be raised by setting the X % value, which serves as a determination criterion, to a value that makes a difference between the cumulative probability distribution obtained with a living body identical to a subject living body of a teacher signal and the cumulative probability distribution obtained with a living body different from the subject living body of the teacher signal sufficiently large. When the value that makes the above-described difference sufficiently large is uncertain, the determination unit 420 may set the X % value to a median value for example, so that X=50%.

After that, the determination unit 420 sets a threshold value $\rho_{min}$ as a second value in advance so as to perform the discrimination and determines whether or not $\rho_{min} \leq \rho(X)$ is satisfied (S23). When $\rho_{min} \leq \rho(X)$ is satisfied (YES in S23), the determination unit 420 determines that the living body 50 is identical to the subject living body (S24). When $\rho_{min} \leq \rho(X)$ is not satisfied, that is, when $\rho_{min} < \rho(X)$ (NO in S23), the determination unit 420 determines that the living body 50 is different from the subject living body (S25). Although the threshold value $\rho_{min}$ needs to be set so that $\rho_{min} \leq \rho(X)$ is satisfied when the living body 50 is identical to the subject living body of the teacher signal, if the setting value is too low, the rate of false detection that a living body different from the subject living body is differentiated as the identical living body rises and thus, the threshold value $\rho_{min}$ needs to be set to a suitable value.

Figure 6:
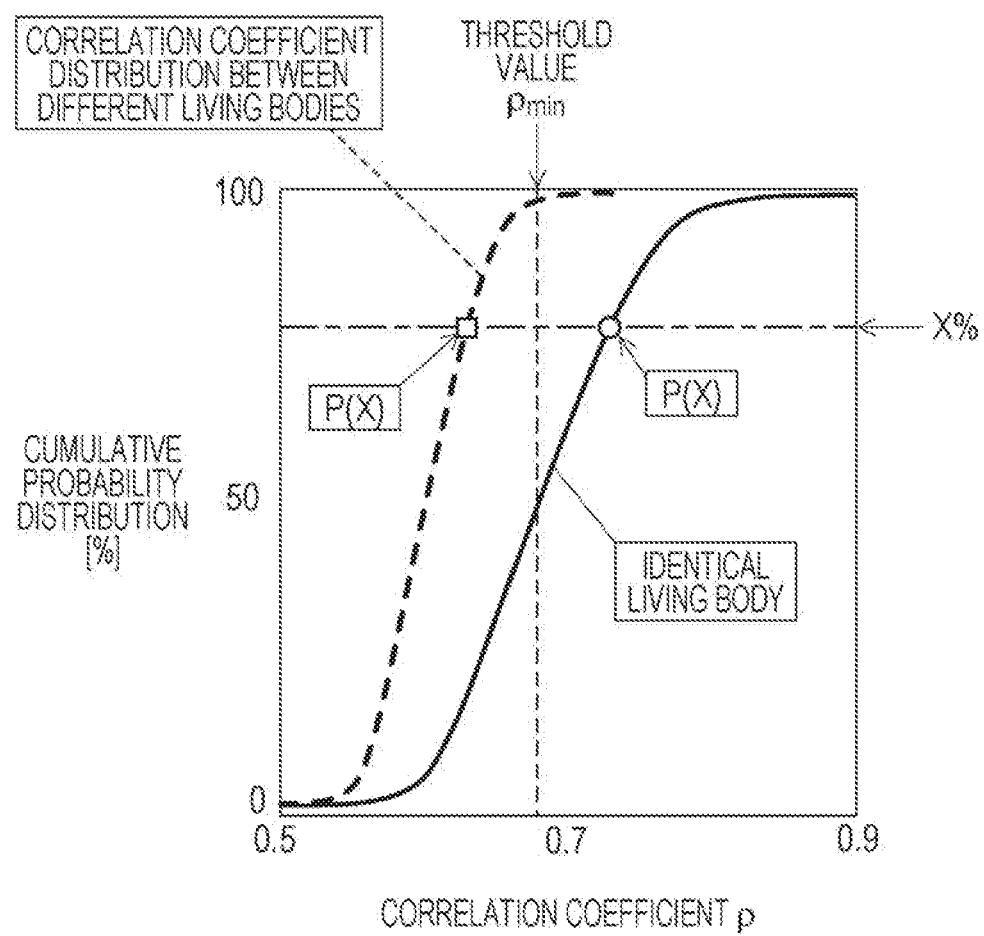
FIG. 6 illustrates graphs that depict a conceptual diagram of cumulative probability distribution of a correlation coefficient.

FIG. 6 illustrates graphs that depict a conceptual diagram of the cumulative probability distribution of the correlation coefficient $\rho$. Specifically, in FIG. 6, the solid-line graph indicates the cumulative probability distribution in a case where the living body is identical to the subject living body of the teacher signal and the broken-line graph indicates the cumulative probability distribution in a case where the living body is different from the subject living body of the teacher signal. Since the correlation coefficient of the identical living body tends to appear as being high, a difference occurs between the correlation coefficients $\rho(X)$ of the distributions indicated by the solid line and the broken line. Learning such a difference in distribution beforehand, for example, by experiment enables the determination unit 420 to perform the determination process using the threshold value $\rho_{min}$ that can reduce false recognition and bring a high recognition rate. The determination unit 420 can perform more desirable discrimination using the threshold value $\rho_{min}$ that is set suitably as described above.

Described next is a discrimination test conducted so as to demonstrate effectiveness of the living body discrimination by the biometric device 10 according to the first embodiment.

Figure 7:
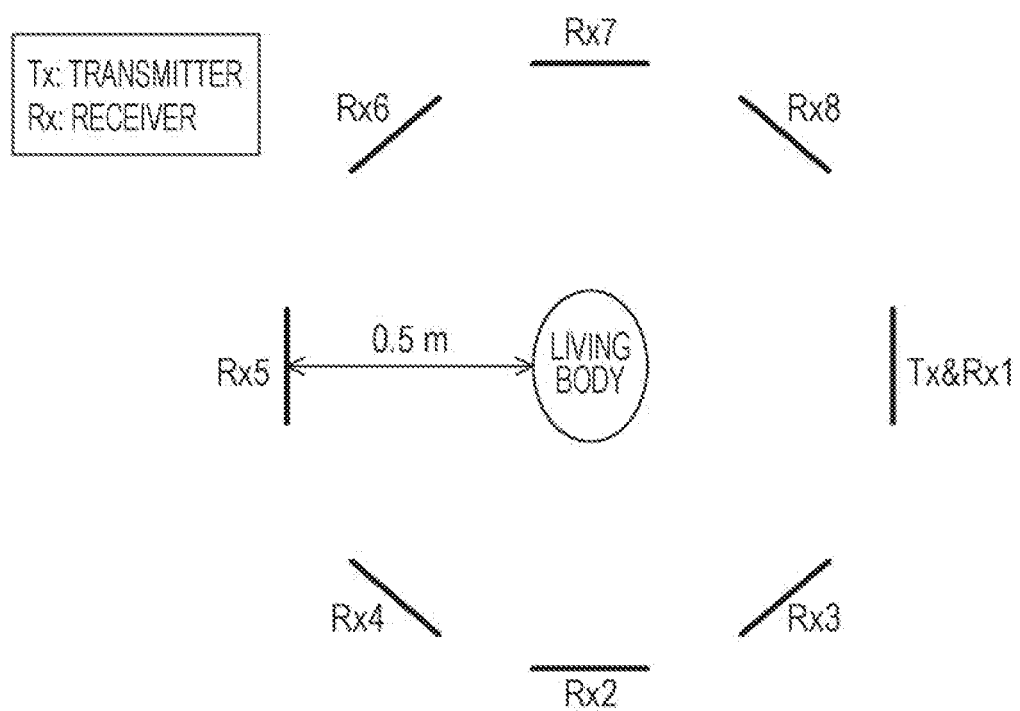
FIG. 7 illustrates an environment used for a discrimination test by the biometric device according to the first embodiment.

FIG. 7 illustrates an environment used for the discrimination test by the biometric device 10 according to the first embodiment.

As illustrated in FIG. 7, the discrimination test uses one transmitter, which corresponds to the transmission unit 20, and eight receivers (reception antennas), which correspond to the reception units 30A to 30H. The eight receivers are arranged at 45-degree spacings in a circle having a radius of 0.5 m, where a living body is located at the center. A transmission antenna element is a square patch antenna of one element and eight respective reception antenna elements of the eight receivers are each a square patch antenna. The height from the floor level to the position at which the reception antenna element is arranged is 0.9 m. The transmission antenna element is arranged immediately above a microwave of the first reception antenna element by one wavelength.

Figure 8:
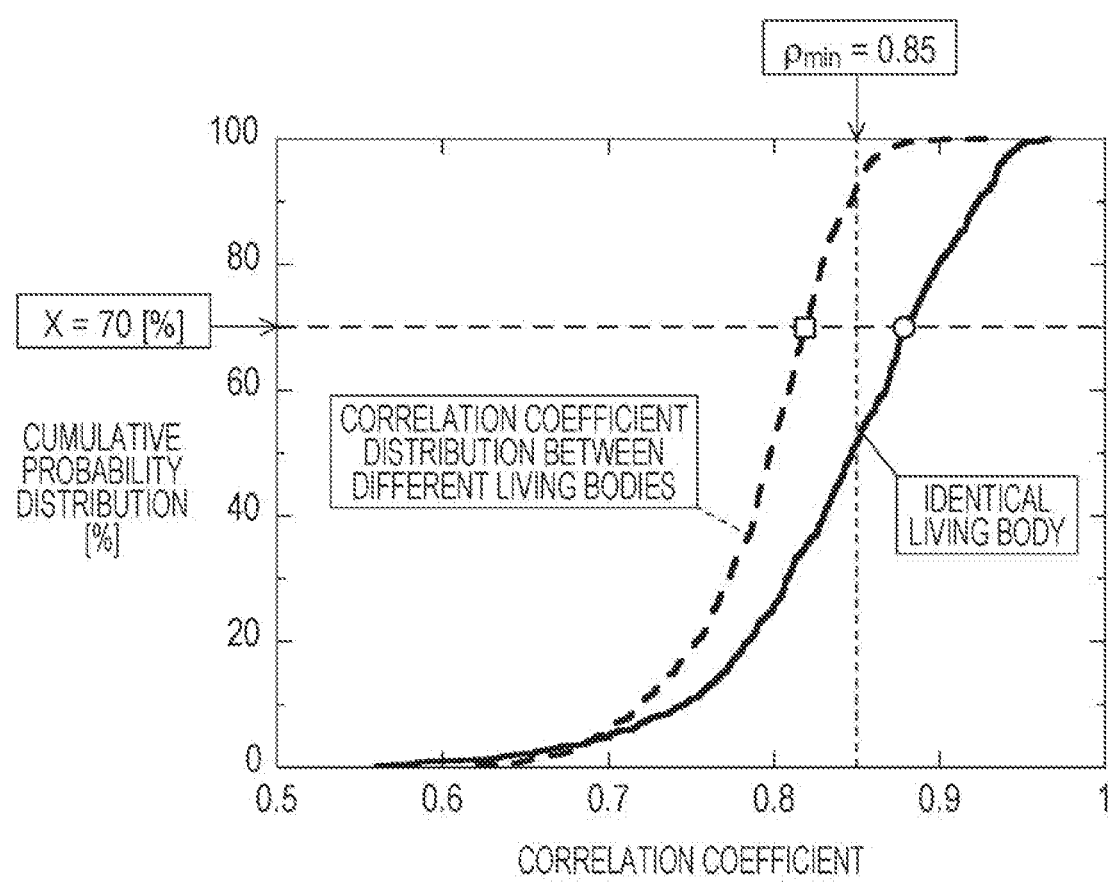
FIG. 8 illustrates cumulative probability distribution of the correlation coefficient obtained through the discrimination test.

FIG. 8 illustrates the cumulative probability distribution of the correlation coefficient $\rho$ obtained through the discrimination test.

The teacher signals here indicate results of performing measurement five times beforehand. The number of observations for the discrimination is one. As for the predetermined period in which the discrimination is performed, T=10 seconds.

It is demonstrated that when the living body is identical to the subject living body, a relatively high correlation coefficient is observed but when the living body is different from the subject living body, the correlation coefficient is low in comparison with a case where the living body is identical to the subject living body. According to the experimental results, the first value that serves as a reference of the comparison of correlation coefficients is set so that X=70 [%], where a difference in distribution is relatively large.

Figure 9:
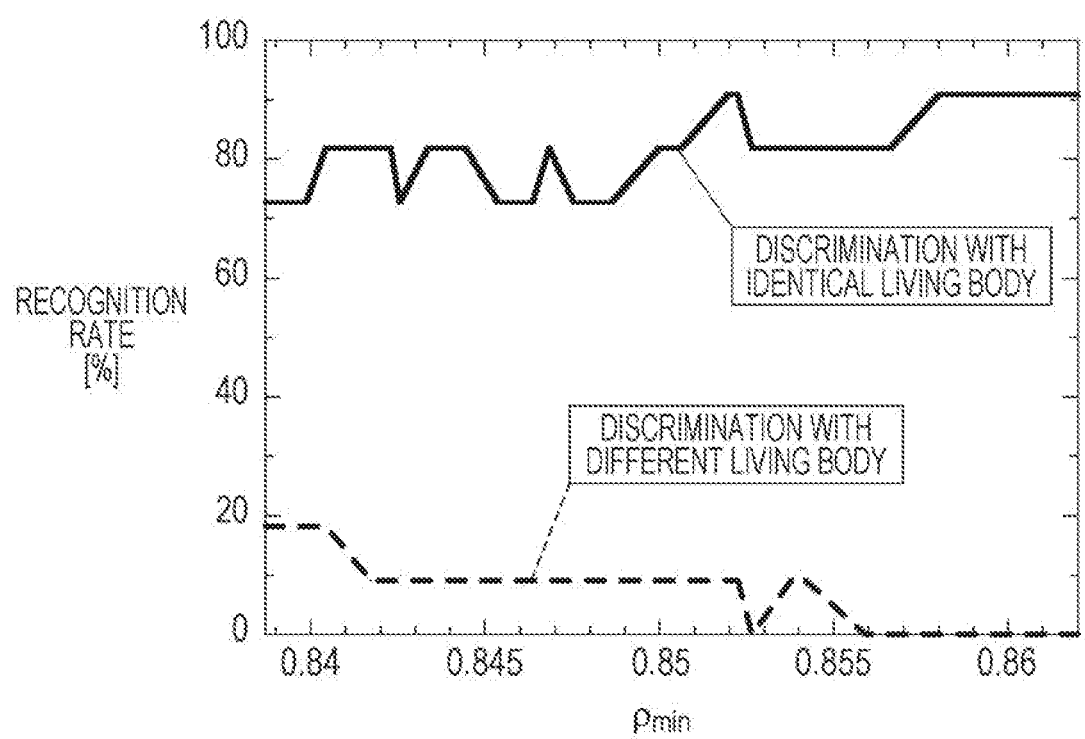
FIG. 9 illustrates results of a discrimination test conducted on the basis of the condition decided according to FIG. 8, X=70 [%]

FIG. 9 illustrates results of a discrimination test conducted on the basis of the condition decided according to FIG. 8, X=70 [%]. In FIG. 9, the solid-line graph indicates a rate of correctly differentiating that the living body is identical to the subject living body when the threshold value $\rho_{min}$ is changed, which is also referred to as the "recognition rate" hereinafter, and the broken-line graph indicates a rate of falsely differentiating a living body different from the subject living body, which is also referred to as the "false recognition rate" hereinafter. The false recognition rate is a rate in a case where in a determination process for a living body different from the subject living body, the living body is determined as being identical to the subject living body.

The broken-line graph in FIG. 9 indicates that the false recognition rate decreases as the threshold value $\rho_{min}$ is raised. It is also demonstrated that setting the threshold value $\rho_{min}$ so that $\rho_{min} \leq 0.86$ enables the false recognition rate to be 0% and the recognition rate to be 90%.

In the biometric device 10 according to the present embodiment, living body discrimination is performed using reception signals received by the N reception units 30A to 30H arranged to surround the periphery of the predetermined range A1. Thus, reception signals can be obtained from a plurality of different angles and living body discrimination can be performed with a small number of times of measurement. As a result, flexibility of living body discrimination can be increased and the living body discrimination can be performed effectively in a short time.

Further, the biometric device 10 according to the present embodiment differentiates a living body, such as a human, using radio signals, such as microwaves. As described above, since a living body, such as a human, can be differentiated without analyzing an image taken with a camera, human discrimination can be performed while human privacy is protected.

First Variation of First Embodiment

Although the biometric device 10 according to the above-described first embodiment includes one transmission unit, 20, and N reception units, 30A to 30H, the present disclosure is not limited to this configuration. For example, as illustrated in FIG. 10, a biometric device 10A that includes N transmission and reception units 60A to 60H, where N is eight in the present variation, may be employed.

Figure 10:
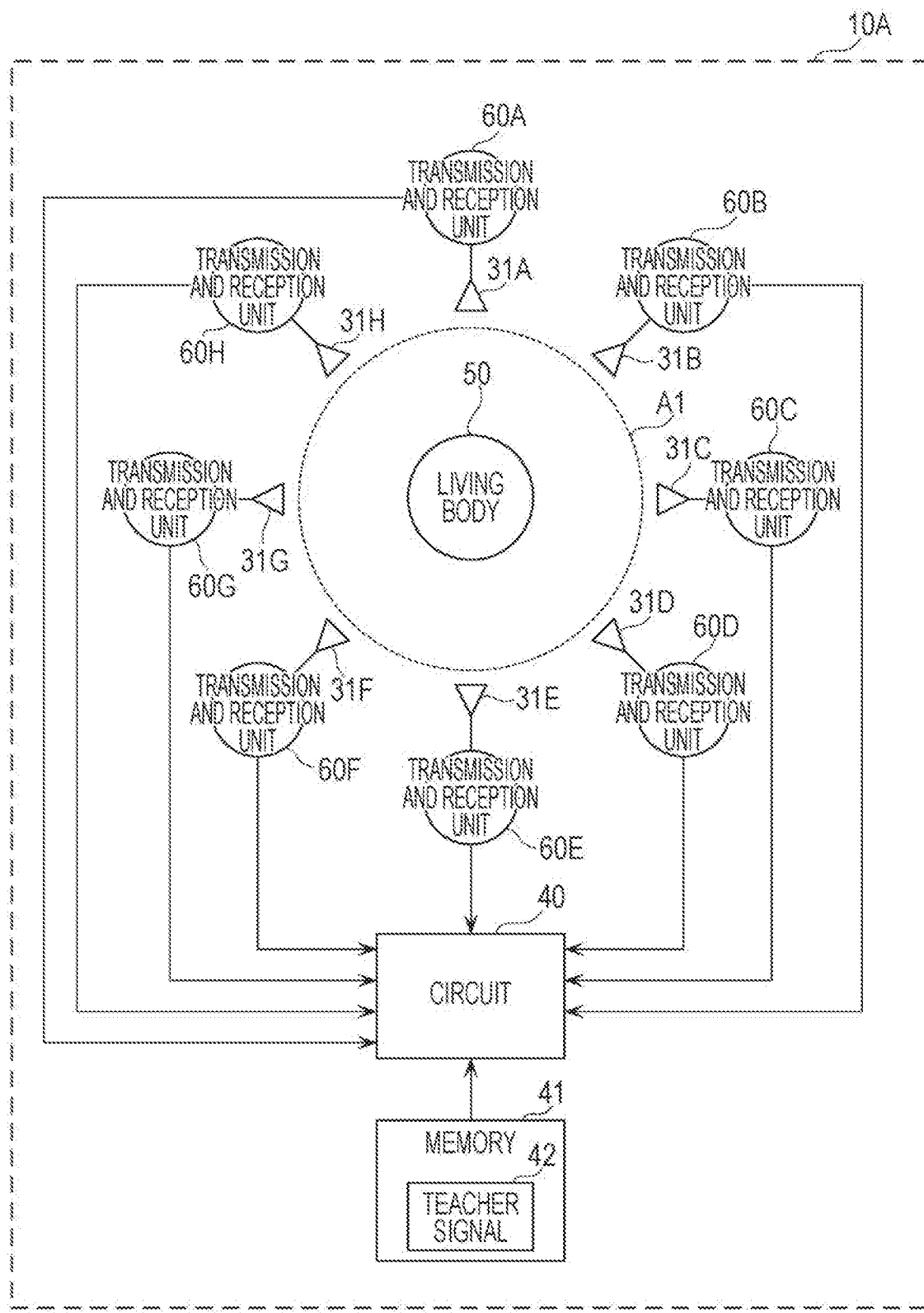
FIG. 10 is a configuration diagram that illustrates an example of a biometric device according to a first variation of the first embodiment.

FIG. 10 is a configuration diagram that illustrates an example of the biometric device 10A according to the first variation.

The transmission and reception units 60A to 60H include N reception antenna elements 31A to 31H. The N reception antenna elements 31A to 31H also function as N transmission antenna elements. The configurations of the circuit 40 and the memory 41 are similar to those in the biometric device 10 according to the first embodiment and thus, the descriptions thereof are omitted.

In this case, each of the transmission and reception units 60A to 60H causes one of the transmission unit and the reception unit to function selectively. That is, for example, a plurality of reception signals are obtained by causing one of the transmission and reception units 60A to 60H to function as a transmission unit and causing the other ones of the plurality of transmission and reception units to function as reception units. The plurality of reception signals based on the transmission signals transmitted from the plurality of transmission and reception units 60A to 60H can be obtained by sequentially switching the transmission and reception units that function as the transmission unit.

Not to mention, this configuration enables the teacher signal and the reception signals to be obtained in a short time efficiently.

Second Variation of First Embodiment

Although the biometric device 10A according to the first variation includes the transmission and reception units that double as the transmission units and the reception units, it is not indispensable for the transmission and reception units to double as the transmission units and the reception units. That is, the biometric device may include a plurality of transmission units and N reception units that are separate from the plurality of transmission units. The plurality of transmission units are arranged to surround the periphery of the predetermined range A1, that is, at positions different from each other outside the predetermined range A1.

Second Embodiment

Although in the biometric devices 10 and 10A according to the first embodiment and the first and second variations thereof described above, the position in the predetermined range A1 at which the living body 50 is located is not taken into account, in a biometric device 10B according to a second embodiment, the position of a living body 50 in a predetermined range A1 may be detected and then discrimination may be performed using the detected position.

Figure 11:
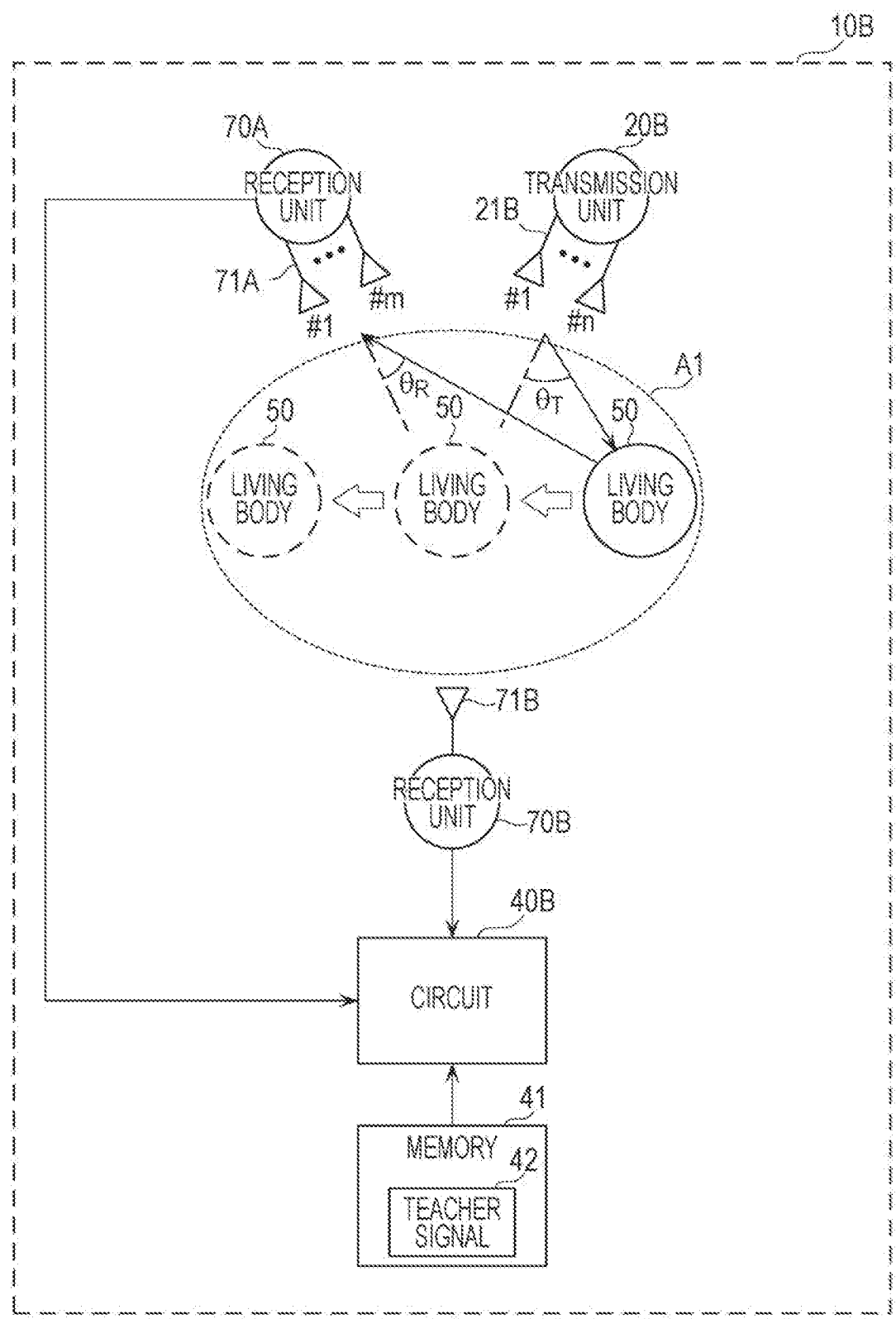
FIG. 11 is a configuration diagram that illustrates an example of a biometric device according to a second embodiment.

FIG. 11 is a configuration diagram that illustrates an example of the biometric device 10B according to the second embodiment.

As illustrated in FIG. 11, the biometric device 10B includes a transmission unit 20B, reception units 70A and 70B, a circuit 40B, and memory 41. The configuration of the memory 41 is similar to that in the first embodiment and thus, the description thereof is omitted.

The transmission unit 20B includes n transmission antenna elements 21B, where n is a natural number larger than or equal to two. The transmission unit 20B includes an array antenna with a configuration where the n transmission antenna elements 21B are arranged side by side in a first predetermined direction on a horizontal plane. Each of the n transmission antenna elements 21B transmits a transmission signal to the predetermined range A1. That is, the transmission unit 20B transmits n transmission signals from n different positions to the predetermined range A1.

Each of the n transmission antenna elements 21B may successively switch and transmit a modulated signal or an unmodulated signal. As described above, by causing the transmission signals transmitted from the n transmission antenna elements 21B to be different from each other for each of the n transmission antenna elements 21B, the transmission antenna element 21B that has transmitted the transmission signal received by the reception unit 70A can be identified. Thus, the transmission unit 20B may include a circuit for performing modulation.

The reception unit 70A includes m reception antenna elements 71A, where m is a natural number larger than or equal to two. The reception unit 70A includes an array antenna with a configuration where the m reception antenna elements 71A are arranged side by side in a second predetermined direction on a horizontal plane. Each of the m reception antenna elements 71A receives n reception signals including reflection signals that are signals included in the n transmission signals and reflected off the living body 50. The reception unit 70A performs frequency conversion on a reception signal constituted of microwaves to convert the signal into the low-frequency signal. The reception unit 70A outputs the signal obtained through the conversion into a low-frequency signal to the circuit 40B. That is, the reception unit 70A may include a circuit for processing a reception signal.

The reception unit 70B includes one reception antenna element 71B. The configuration of the reception unit 70B is the same as that of one of the reception units 30A to 30H according to the first embodiment and thus, the description thereof is omitted. The reception unit 70B is arranged at a position opposite the positions at which the transmission unit 20B and the reception unit 70A are arranged across the predetermined range A1. That is, the reception unit 70A and the reception unit 70B are arranged to surround the periphery of the predetermined range A1.

A hardware configuration of the circuit 40B is the same as that of the circuit 40 according to the first embodiment and thus, the description thereof is omitted.

A functional configuration of the circuit 40B is described below by referring to FIG. 12.

Figure 12:
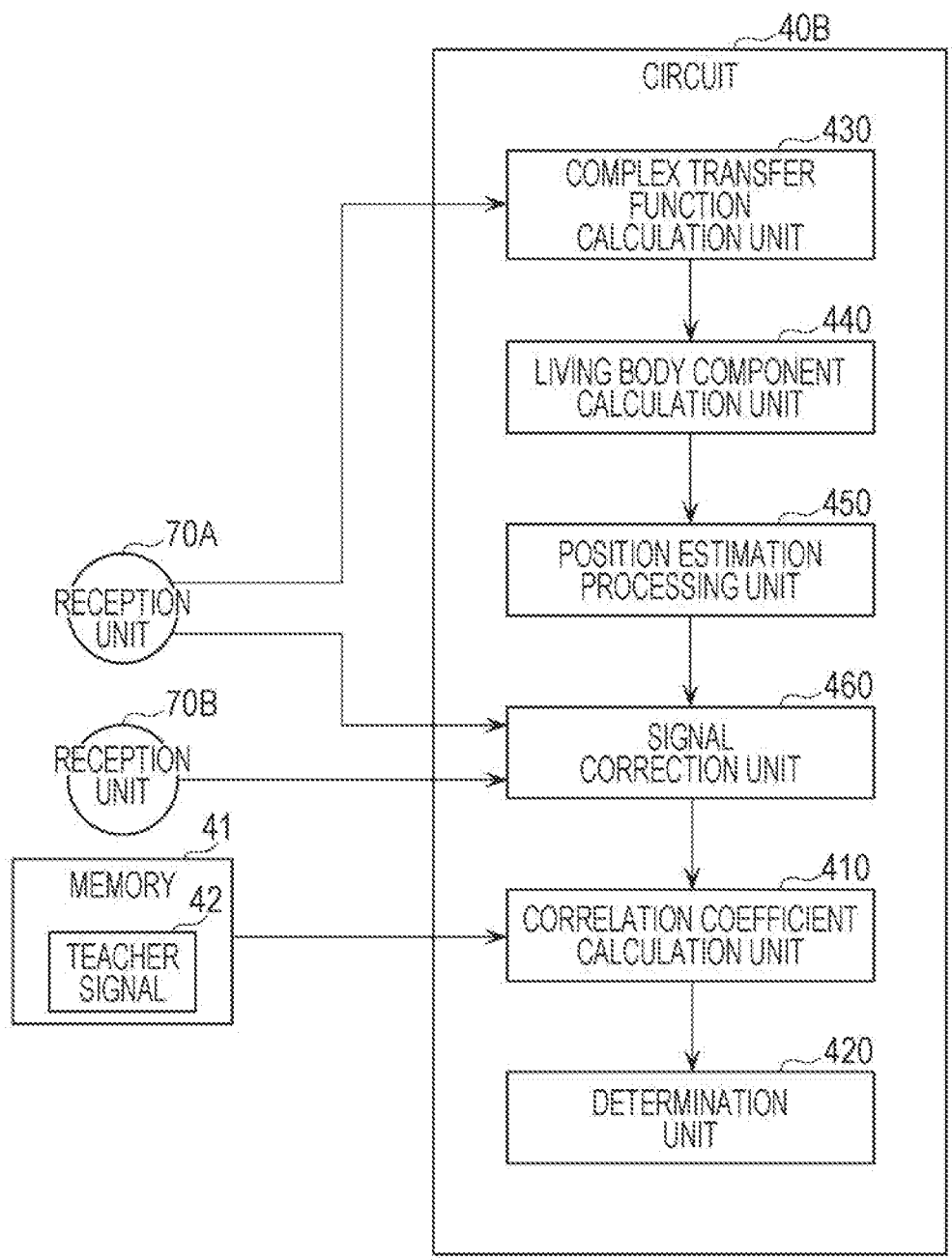
FIG. 12 is a block diagram that illustrates functional configurations of a circuit and memory according to the second embodiment.

FIG. 12 is a block diagram that illustrates the functional configurations of the circuit 40B and the memory 41 according to the second embodiment.

The circuit 40B includes a correlation coefficient calculation unit 410, a determination unit 420, a complex transfer function calculation unit 430, a living body component calculation unit 440, a position estimation processing unit 450, and a signal correction unit 460. The circuit 40B is different from the circuit 40 according to the first embodiment in that the complex transfer function calculation unit 430, the living body component calculation unit 440, the position estimation processing unit 450, and the signal correction unit 460 are further included and the configurations thereof are described below.

The complex transfer function calculation unit 430 calculates a complex transfer function from a reception signal converted into a low-frequency signal. The complex transfer function indicates propagation loss and phase rotation between each of the transmission antenna elements 21B and each of the reception antenna elements 71A. When the number of transmission antenna elements is n and the number of reception antenna elements is m, the complex transfer function indicates a complex matrix having m×n components. Hereinafter, this complex matrix is referred to as the complex transfer function matrix. The calculated complex transfer function matrix is output to the living body component calculation unit 440. That is, according to each of the plurality of reception signals received at each of the m reception antenna elements 71A during a predetermined period, the complex transfer function calculation unit 430 calculates a first matrix of n×m whose components are respective complex transfer functions indicating propagation characteristics between each of the n transmission antenna elements 21B and each of the m reception antenna elements 71A.

The living body component calculation unit 440 separates the complex transfer function matrix components into the complex transfer function matrix components obtained from the reception signals via the living body 50 and the complex transfer function matrix components obtained from the reception signals not via the living body 50. The components via the living body 50 are components that vary with time according to living body activities. So, when the people or things other than the living body 50 are still, the components via the living body 50 can be extracted by taking the components other than direct current out of the components obtained by performing Fourier transform on the complex transfer function matrix components in a time direction. Also, the components via the living body 50 can be extracted by for example, taking out components where a difference from the result observed when the living body 50 is not present in the predetermined range A1 exceeds a predetermined threshold value. As described above, by extracting the complex transfer function matrix components obtained from the reception signals including the reflection signals via the living body 50, the living body component calculation unit 440 calculates the extracted complex transfer function matrix components as living body components. That is, by extracting a second matrix corresponding a predetermined frequency range in the first matrix, the living body component calculation unit 440 extracts the second matrix corresponding components affected by vital activities that include at least any of the respiration, cardiac beats, and body movement of a living body. The predetermined frequency range corresponds to for example, frequencies derived from the above-described vital activities that include at least any of the respiration, cardiac beats, and body movement of the living body. The predetermined frequency range corresponds to for example, frequencies in a range from 0.1 Hz to 3 Hz inclusive. Thus, living body components affected by vital activities of a body part of the living body 50 based on the movement of the heart, lungs, diaphragm, and internal organs, or by vital activities by a hand, a foot, or the like can be extracted. Examples of the body part of the living body 50 based on the movement of the heart, lungs, diaphragm, and internal organs include the pit of the stomach of a human.

The living body components here constitute a matrix with m×n components and are extracted from the complex transfer functions obtained from the reception signals observed in the reception unit 70A during a predetermined period. Thus, the living body components include frequency responses or time response information. The predetermined period is a period that is approximately half of at least one cycle of the respiration, cardiac beats, and body movement of a living body.

The living body components calculated in the living body component calculation unit 440 are output to the position estimation processing unit 450. The position estimation processing unit 450 estimates the position of the living body 50 using the calculated living body components. That is, the position estimation processing unit 450 estimates a position in the predetermined range A1 at which the living body 50 is present by estimating the position of the living body 50 relative to the biometric device 10B using the second matrix. In the position estimation, both of a departure angle $\theta_\tau$ from the transmission unit 20B and an arrival angle $\theta_R$ to the reception unit 70A are estimated and the position of the living body 50 is estimated by trigonometry according to the estimated departure angle $\theta_\tau$ and arrival angle $\theta_R$, and the positions of the transmission unit 20B and the reception unit 70A, which are stored in the memory 41 in advance.

The departure angle $\theta_\tau$ is an angle formed by a first reference direction set as desired with respect to the transmission unit 20B and a first living body direction, which is a direction from the transmission unit 20B to the living body 50. Similarly, the arrival angle $\theta_R$ is an angle formed by a second reference direction set as desired with respect to the reception unit 70A and a second living body direction, which is a direction from the reception unit 70A to the living body 50. The first reference direction, the first living body direction, the second reference direction, and the second living body direction are directions on a horizontal plane.

The signal correction unit 460 corrects each of the plurality of reception signals received by the reception units 70A and 70B according to the position of the living body 50 estimated by the position estimation processing unit 450 while taking the distances between the transmission antenna elements 21B, the reception antenna elements 71A and 71B, and the living body 50 into account.

The correlation coefficient calculation unit 410 calculates a plurality of correlation coefficients by comparing the teacher signal 42 stored in the memory 41 and a plurality of correction signals obtained through the correction by the signal correction unit 460. The correlation coefficient calculation unit 410 is different from that according to the first embodiment only in that a plurality of correction signals are used instead of a plurality of reception signals and the processes executed by the correlation coefficient calculation unit 410 are similar to those in the first embodiment.

Figure 13:
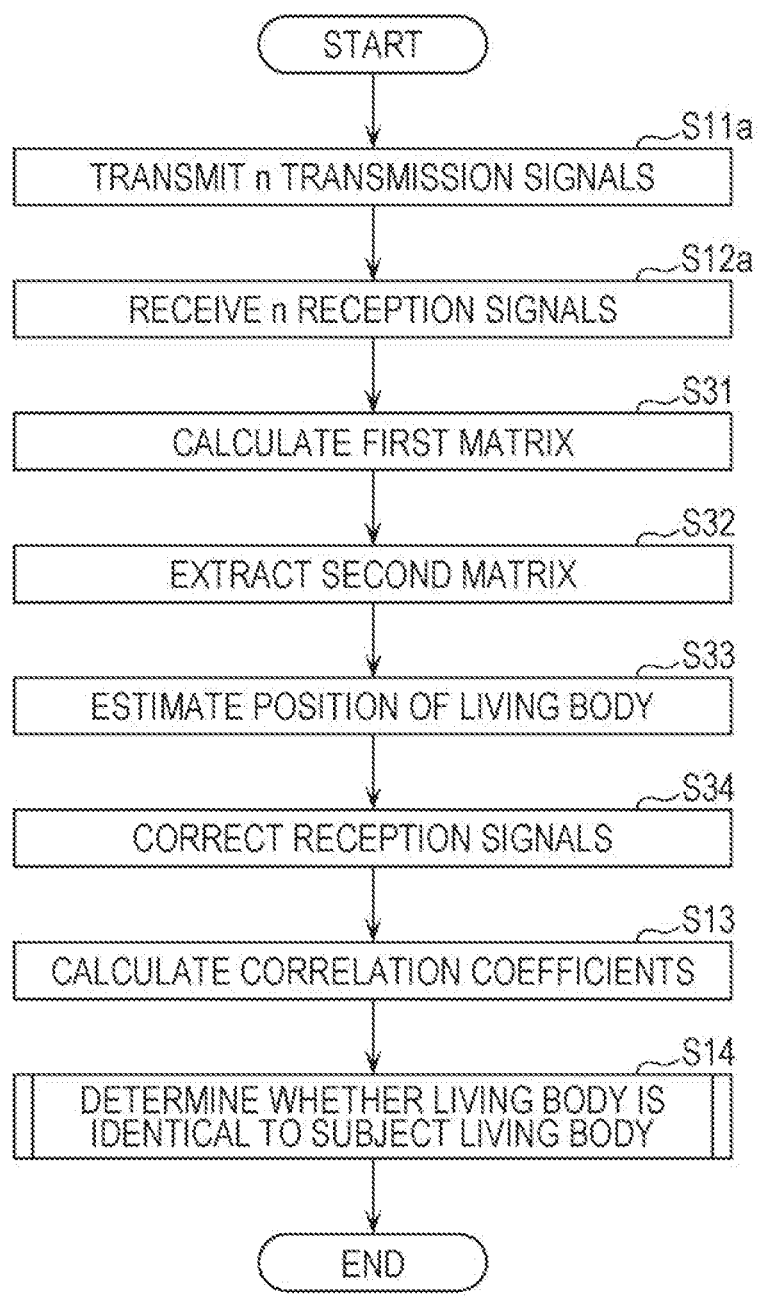
FIG. 13 is a flow chart that illustrates an example of operations of the biometric device according to the second embodiment.

FIG. 13 is a flow chart that illustrates an example of operations of the biometric device 10B according to the second embodiment.

In the biometric device 10B, while the living body 50 is located in the predetermined range A1, n transmission signals are transmitted from the transmission antenna elements 21B to the predetermined range A1 (S11a).

The reception units 70A and 70B receive the n reception signals including a plurality of reflection signals, which result from the n transmission signals transmitted from the transmission unit 20B and then reflected off the living body 50, using the respective reception antenna elements 71A and 71B of the reception units 70A and 70B (S12a).

According to each of the plurality of reception signals received at each of the m reception antenna elements 71A during a predetermined period, the circuit 40B calculates the first matrix of n×m whose components are respective complex transfer functions indicating propagation characteristics between each of the n transmission antenna elements 21B and each of the m reception antenna elements 71A (S31).

By extracting the second matrix corresponding a predetermined frequency range in the first matrix, the circuit 40B extracts the second matrix corresponding components affected by vital activities that include at least any of the respiration, cardiac beats, and body movement of the living body 50 (S32).

Using the second matrix, the circuit 40B estimates the position at which the living body 50 is present relative to the biometric device 10B (S33).

The circuit 40B corrects each of the plurality of reception signals received by the reception units 70A and 70B according to the estimated position of the living body 50 (S34).

The circuit 40B performs steps S13 and S14 described in the first embodiment and ends the process.

In the biometric device 10B according to the present embodiment, even when the living body 50 is moving in the predetermined range A1, the position of the moving living body 50 is measured and on the basis of the coordinates of the measured position, the distance between the reception units and the living body and the directions are calculated to correct the reception signals and accordingly, living body discrimination can be performed even on the living body 50 that is moving.

Variation of Second Embodiment

Although in the above-described second embodiment, the position of the living body 50 in the predetermined range A1 is estimated using the n reception signals including the plurality of reflection signals resulting from the transmission signals transmitted by the transmission unit 20B and then reflected off the living body 50, the present disclosure is not limited thereto. For example, the position of the living body 50 in the predetermined range A1 may be detected by using a device that can measure the position of a living body, such as an existing living body radar or camera.

In each of the above-described embodiments, each constituent may be constituted with dedicated hardware or may be implemented by executing a software program suitable each constituent. Each constituent may be implemented by a program execution unit, such as a central processing unit (CPU) or a processor, reading a software program recorded in a recording medium, such as a hard disk or semiconductor memory, and executing the software program. The software to implement the biometric device and the like according to each of the above-described embodiments is a program described below.

That is, the program causes a computer to execute a method of differentiating a living body using a biometric device that includes at least one transmission antenna element, N receivers, memory, and a circuit, the N receivers including respective reception antenna elements, the method including: transmitting a transmission signal to a predetermined range including the living body using the at least one transmission antenna element; receiving N reception signals including a reflection signal resulting from the transmission signal reflected off the living body using the respective reception antenna elements of the N receivers during a predetermined period; reading a teacher signal out of the memory, the teacher signal being constituted of N reception signals obtained by the N receivers receiving in advance reception signals including a reflection signal resulting from a transmission signal that is transmitted from the at least one transmission antenna element to a subject living body and then reflected off the subject living body; calculating a plurality of correlation coefficients according to the teacher signal and the N reception signals received by the N receivers; and determining that the living body and the subject living body are identical to each other when a predetermined correlation coefficient included in the plurality of correlation coefficients is included in a predetermined value range.

Although the biometric devices 10, 10A, and 10B according to one or more aspects of the present disclosure are described above on the basis of the embodiments, the present disclosure is not limited to the embodiments. As long as the spirit of the present disclosure is not departed, an embodiment in which various changes that those skilled in the art can conceive are added to the present embodiments or an embodiment formulated by combining constituents in different embodiments may also be included in the scope of the one or more aspects of the present disclosure.

The present disclosure can be utilized for biometric devices that differentiate living bodies using radio signals and can be utilized particularly for living body biometric devices and the like installed in for example, household appliances that perform control according to living bodies or monitoring devices that detect intrusion of living bodies.

What is claimed is:

1. A device that differentiates a living body, the device comprising:
    a circuit that performs,
        acquiring first N reception signals, each of the first N reception signals has been received at a respective one receiver out of N receivers, which are arranged to surround a periphery of a predetermined range, using respective reception antenna elements of the N receivers during a predetermined period,
        calculating a plurality of correlation coefficients based on a teacher signal, stored in the memory, and the first N reception signals, and
        determining that the living body and a subject living body are identical to each other when a correlation coefficient included in the plurality of correlation coefficients, is included in a predetermined value range,
    wherein,
        the first N reception signals including a reflection signal resulting from a first transmission signal reflected off the living body,
        the first transmission signal being transmitted from at least one transmission antenna element to a predetermined range including the living body, and
        the teacher signal being constituted of second N reception signals, which had been obtained by the N receivers, the second N reception signals including a reflection signal resulting from a second transmission signal reflected off the subject living body, the second transmission signal being transmitted from the at least one transmission antenna element to the subject living body.

2. The device according to claim 1, wherein
    the circuit further
        calculates a cumulative distribution function with respect to the plurality of correlation coefficients, and
        determines that the living body and the subject living body are identical to each other when a correlation coefficient that is included in the plurality of correlation coefficients and has a cumulative percentage that indicates a first value in the cumulative distribution function is included in a value range not less than a second value and not more than a third value.

3. The device according to claim 1, wherein
the circuit calculates a plurality of correlation coefficients between the teacher signal and each of the first N reception signals as the plurality of correlation coefficients by sliding correlation operation.

4. The device according to claim 1, wherein
the circuit further
estimates a position of the living body in the predetermined range using the first N reception signals, and
calculates the plurality of correlation coefficients using the position of the living body.

5. The device according to claim 1, wherein
the at least one transmission antenna element includes a plurality of transmission antenna elements, and
the plurality of transmission antenna elements are arranged at positions different from each other.

6. The device according to claim 1, wherein
the at least one transmission antenna element includes N transmission antenna elements,
the N reception antenna elements are respectively the N transmission antenna elements, and
the circuit further
estimates a position of the living body in the predetermined range using the first N reception signals, and
calculates the plurality of correlation coefficients using the position of the living body.

7. The device according to claim 1, wherein
the teacher signal is constituted of the second N reception signals obtained by the N receivers receiving the reception signals during a period that is K times as long as the predetermined period, where K is two or more.

8. A method of differentiating a living body using a device that includes memory, and a circuit, the method comprising:
acquiring first N reception signals, each of the first N reception signals has been received a at respective one receiver out of N receivers, which are arranged to surround a periphery of a predetermined range, using respective reception antenna elements of the N receivers during a predetermined period,
reading a teacher signal out of the memory;
calculating a plurality of correlation coefficients based on the teacher signal and the acquired first N reception signals; and
determining that the living body and the subject living body are identical to each other when a predetermined correlation coefficient, included in the plurality of correlation coefficients, is included in a predetermined value range;
wherein,
the first N reception signals including a reflection signal resulting from a first transmission signal reflected off the living body,
the first transmission signal being transmitted from at least one transmission antenna element to a predetermined range including the living body, and
the teacher signal being constituted of second N reception signals, which had been obtained by the N receivers, the second N reception signals including a reflection signal resulting from a second transmission signal reflected off the subject living body, the second transmission signal being transmitted from the at least one transmission antenna element to the subject living body.

* * * * *